United States Patent [19]

Edwards, Jr. et al.

[11] 4,421,120

[45] Dec. 20, 1983

[54] PEAK RESPIRATORY FLOW MONITOR

[75] Inventors: Rodney Edwards, Jr., Framingham; John W. Burke, Jr., Melrose; Peter Gazzara, Reading, all of Mass.

[73] Assignee: Biotrine Corporation, Woburn, Mass.

[21] Appl. No.: 239,272

[22] Filed: Mar. 2, 1981

[51] Int. Cl.³ .............................................. A61B 5/02
[52] U.S. Cl. .................................................. 128/725
[58] Field of Search ............... 128/716, 725, 726, 727; 604/51–53; 46/178, 179, 180; 272/99

[56] References Cited

U.S. PATENT DOCUMENTS

| | | | |
|---|---|---|---|
| 2,505,141 | 4/1950 | Pitts | 46/179 |
| 2,908,244 | 10/1959 | Clark | 46/179 |
| 2,915,851 | 12/1959 | Ringman | 46/180 |
| 3,298,362 | 1/1967 | Lippitt, Jr. et al. | 272/99 |
| 3,367,324 | 2/1968 | DeBono | 46/179 |
| 3,949,738 | 4/1976 | Monroe | 128/725 |

FOREIGN PATENT DOCUMENTS 2030775 12/1971 Fed. Rep. of Germany ...... 128/725
2379291 10/1978 France ............................... 272/99

OTHER PUBLICATIONS

"A Whistle for Testing Lung Function" *The Lancet* 11/30/63, DeBono, pp. 1146, 1147.

*Primary Examiner*—Richard J. Apley
*Assistant Examiner*—T. J. Wallen
*Attorney, Agent, or Firm*—Bromberg, Sunstein & McGregor

[57] ABSTRACT

A peak respiratory flow monitor utilizes an enclosure having a series of openings through the wall thereof, a provision for covering a desired number of these openings, and a provision for generating a signal when the air flow through the enclosure reaches a threshold. In a preferred embodiment the enclosure includes an elongated tubular member, and the threshold indicator is a reed placed in a chamber that has an adjustable valve for calibrating the flow past the reed. Furthermore, the chamber causes a displacement of flow from along the longitudinal axis of the tubular member.

6 Claims, 5 Drawing Figures

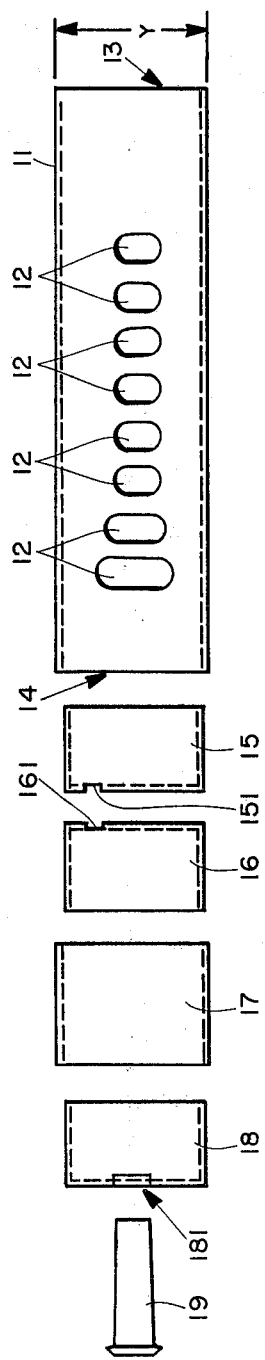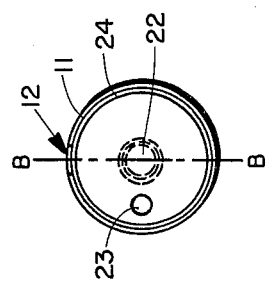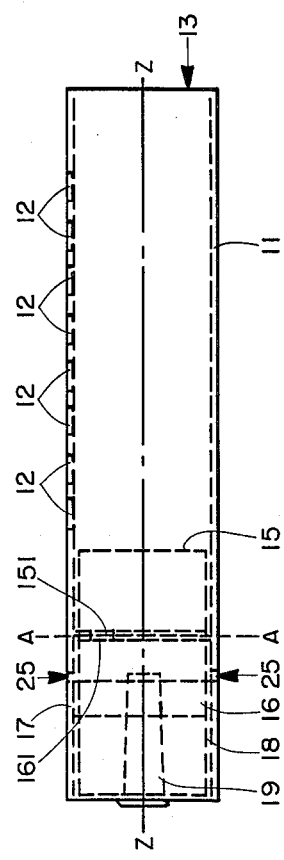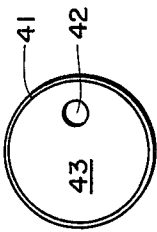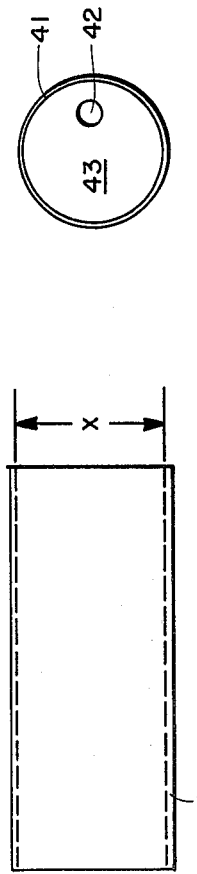

PEAK RESPIRATORY FLOW MONITOR

DESCRIPTION

1. Technical Field

This invention relates to a device for monitoring the peak respiratory flow of a subject, and more particularly to a peak respiratory flow monitor of simple mechanical construction.

2. Background Art

Devices for measuring pulmonary function of a subject are common in the prior art. Although most devices are relatively complicated, such as disclosed in U.S. Pat. No. 3,687,130, there are a number of mechanical devices for measuring the peak flow rate of a single forced expiration. The devices disclosed in U.S. Pat. Nos. 3,635,214, 3,958,565, and 4,041,935 all utilize the displacement of a piston under controlled circumstances as the method for indicating pulmonary function. U.S. Pat. No. 3,949,738 discloses a device that utilizes, instead of a piston, a series of openings in ach of which a liquid is held by surface tension in a film and, in accordance with the extent of peak flow through the device, the film of appropriate openings is broken sequentially to indicate peak flow. Finally, a peak expiratory flow measurement device is disclosed in E. F. deBono, "A whistle for testing lung function," *The Lancet,* Vol. 2 (63) No. 7318, Nov. 30, 1963, pp. 1146-1147. The deBono device utilizes a double-orifice whistle (as that of a tea kettle) placed at the end of a tube; the subject blows in at the other end of the tube, and an adjustment is provided by a longitudinal slot placed in the wall of the tube, which can be covered up an adjustable amount by a sleeve fitting around the tube. We have disclosed a device, similar to that of deBono, that utilizes a reed placed axially and directly in the line of flow through the tube with an adjustable slot at the end of the tube.

A particular problem with prior art devices is to provide consistent results from one device to the next, and furthermore to have each device behave in a manner that is precise and repeatable for a given flow. For example, the deBono device may be difficult to use for determining whether flow has reached a given threshold, owing to the nature of the whistle employed, which does not have a loud and distinct threshold. On the other hand, our prior reed device, although providing a clear threshold, suffered from the risk that the threshold of one reed in a given device may not occur at the same flow as the threshold of another reed in another unit.

SUMMARY OF THE INVENTION

The present invention utilizes an elongated tubular member having a series of openings through the wall thereof, a provision for covering a desired number of these openings, and a provision for generating an audible signal when the air flow through the length of the tubular member reaches a threshold. In a preferred embodiment the threshold indicator is a reed placed at the rear end of the tubular member. The reed is then placed in a chamber that has an adjustable valve for calibrating the flow past the reed. Furthermore, the chamber causes a displacement of flow from along the longitudinal axis of the tubular member. Also, the openings in the tubular member are placed along its length and are selectively covered by a sleeve that is capable of sliding along the tubular member.

BRIEF DESCRIPTION OF THE DRAWINGS

FIG. 1 shows an exploded longitudinal section of a preferred embodiment of the invention;

FIG. 2A shows an assembled longitudinal section of the embodiment shown in FIG. 1, wherein the monitor has been rotated ninety degrees about axis Z—Z;

FIG. 2B shows a cross section of the same embodiment, taken through plane A—A of FIG. 2A;

FIG. 3 illustrates a sleeve for use with the embodiment shown in FIGS. 1 and 2; and FIG. 4 shows detail of the baffle pieces 15 and 16 shown in FIGS. 1 and 2.

DESCRIPTION OF SPECIFIC EMBODIMENTS

An exploded longitudinal section of the present invention is shown in FIG. 1. The elongated tubular member 11 is typically about four and one half inches long. In it are provided a series of openings 12 that are individually designed to provide appropriate intervals of flow rate, for example, in liters per second or liters per minute. Because the device is not inherently linear over the actual flow range desired, it should be noted that the holes are not of uniform size. The tube in this embodiment is made out of cardboard having a thickness of approximately 0.04 inches and an inner diameter of 1 1/16 inches. The front end 13 of the tube serves as a mouthpiece, and the rear end 14 receives baffle piece 15. The baffle pieces 15 and 16 are in fact identically shaped plastic items. Each piece includes a short tubular section open at one end and closed at the other end, except that the closed end is provided with an aperture. The aperture of piece 15 is shown as item 151, and the aperture of piece 16 is shown as opening 161. The centers of these apertures are placed at a distance from the longitudinal axis of the monitor. It can be seen that items 15 and 16 are oriented so that their closed ends face each other.

Item 16 of FIG. 1 is placed in the whistle chamber tube 17. Also placed in this tube is end piece 18. The piece 18 is identical in construction to baffle piece 15 and 16, except that its closed end is provided with a hole 181 that is axially located in lieu of any other aperture. In this hole is placed the reed assembly 19. The reed assembly includes a vibrating metal reed that makes an audible sound when flow through the assembly reaches a flow of a determined rate.

FIG. 2A, an assembled longitudinal section shows the relation of the various components as mounted. Piece 15 is recessed in the tubular member 11, and glued in place. Piece 16 is glued in chamber tube 17 in such a way as to protrude from the tube in which it is glued. As a result, the protruding portion of piece 16 can be inserted into sleeve 11 in such a way that the surfaces of the baffle pieces 15 and 16 come into direct contact at plane A—A. When chamber tube 17 is properly rotated, baffle piece 16 will rotate with it, and the apertures 151 and 161 in the baffle pieces can thereby be made to be in complete coincidence or partial coincidence as desired. When the desired orientation of the apertures 151 and 161 has been achieved, the relation of the tube 17 to the tubular member 11 can be fixed by placing a piece of tape around the boundary 25 between the two tubes, or by other suitable means, thereby securing the relationship between apertures 151 and 161. The end piece 18 is also glued into the chamber tube 17. The reed assembly 19 may be force-fitted or otherwise fixed in the end piece 18 through the hole 181.

An examination of FIG. 2A will reveal that although flow begins axially at the front end 13 along the axis Z—Z, the flow is displaced through apertures 151 and 161 as it enters the whistle chamber formed by baffle piece 16, end piece 18, and tube 17. We have found that the displacement of this flow prevents problems in accuracy that occur when flow is directed simply axially through the reed. The displacement of axial flow could be provided by other means, such as placement of a cap, over the reed, with the cap having entry holes only off-axis. Since reeds may have different threshholds, the device may be calibrated by putting a known flow through the device with a known number of apertures 12 covered and then rotating tube 17 with respect to tubular member 11 until the relation of apertures 151 and 161 is skewed to the point that the desired amount of flow reduction into the chamber in which the reed is placed has occurred. In this fashion the baffle pieces 15 and 16, in their motion relative to one another, act as a valve to regulate flow through the monitor.

FIG. 2B is a cross section taken at plane A—A of FIG. 2A. Item 23 is the coincidentally located apertures 151 and 161. Item 22 shows in dotted fashion the location of the reed assembly 19, and the hole 181 in which it is placed. Item 24 is the thickness of the walls of the baffle pieces 15 and 16. Also shown are relative locations of the apertures 12 and the tubular member 11. FIG. 2A is taken through the plane B—B of FIG. 2B.

FIG. 3 illustrates a sleeve for use in covering a desired number of holes 12 of the monitor illustrated in the previous figures. The inner diameter X—X of the sleeve 31 must be equal to or slightly greater than the outer diameter Y—Y of the tubular member 11 illustrated in FIG. 1. Preferably the sleeve 31 fits snugly over the tubular member 11 so as to prevent unwanted leakage through those holes 12 covered by the sleeve.

FIG. 4 illustrates the baffle pieces 15 and 16. Each piece includes a wall 41, and has a covered end 43 in which is placed an aperture 42 the center of which is located a distance away from the central axis of the piece.

Although the present invention is described for use in measuring peak flow on expiration, it may be utilized in measuring peak inspiratory flow also, provided the reed assembly includes a reed operable on flow in the reverse direction, and provided the instrument is suitably calibrated for such flow.

Accordingly, while the invention has been described with particular reference to specific embodiments, it will be understood that it may be embodied in a variety of forms diverse from those shown and described without departing from the spirit and scope of the invention as described by the following claims.

What is claimed is:

1. A peak respiratory flow monitor comprising:
   (a) an enclosure, having (i) a front end serving as an air input port, (ii) a series of openings through the wall of the enclosure, (iii) an input flow axis, passing through the center of the input port, in the direction of air flow at the air input;
   (b) means for covering a desired number of the openings; and
   (c) means, having an air flow input, for generating a signal when the air flow therethrough reaches a threshold, such means being called below "the whistle" and wherein the whistle includes a reed and means for causing displacement of air flow, from the input flow axis, prior to flowing along the reed.

2. A monitor in accordance with claim 1, further comprising:
   a valve for regulating flow through the input of the whistle.

3. A peak respiratory flow monitor comprising:
   (a) an elongated tubular member, having (i) a front end serving as an air input port, (ii) a series of openings through the wall of the tubular member, (iii) an input flow axis, passing through the center of the input port, in the direction of air flow at the air input, and (iv) a rear end opposite to the front end;
   (b) means for covering a desired number of the openings; and
   (c) means, having an air flow input, for generating a signal when the air flow therethrough reaches a threshold, such means being called below "the whistle", wherein the whistle includes a reed and means for causing displacement of air flow, from the input flow axis, prior to flowing along the reed, and also includes a chamber, in which the reed is mounted, such chamber having a flow input, being the whistle input, which is mounted proximate to the rear end of the tubular member, such whistle input including a first baffle disposed transversely to the longitudinal axis of the tubular member, such baffle having an aperture the center of which is located off the longitudinal axis; and
   (d) a valve for regulating flow through the input of the whistle.

4. A monitor in accordance with claim 3, wherein (i) the first baffle is at right angles to the longitudinal axis and (ii) the valve includes a second baffle, placed proximate to the rear end of the tubular member and in front of the first baffle, such second baffle having an aperture the center of which is located off the longitudinal axis.

5. A monitor in accordance with claim 4, wherein the center of the aperture in the first baffle is located off the longitudinal axis by a distance approximately equal to the distance by which the center of the aperture in the second baffle is located off the longitudinal axis.

6. A monitor in accordance with claim 5, wherein the openings are placed along the length of the tubular member and the means for covering a desired number of the openings includes a tubular sleeve, placed concentrically around the tubular member, for sliding along the tubular member.

* * * * *